United States Patent [19]

King et al.

[11] Patent Number: 5,952,535
[45] Date of Patent: *Sep. 14, 1999

[54] SELECTIVE CATALYTIC CONVERSION OF A $C_9$ AROMATIC FEEDSTOCK CONTAINING SUBSTANTIAL AMOUNTS OF ETHYL SUBSTITUTED AROMATIC COMPONENTS TO A PRODUCT RICH IN TOLUENE AND/OR XYLENES

[75] Inventors: David L. King, Mountain View, Calif.; Eric G. Derouane, Liverpool, United Kingdom; Jacques C. DeDeken, Palo Alto, Calif.; Toshihiko Masuda, Sagamihara; Shinji Nishikawa, Kawasaki, both of Japan; Hiroshi Fujii, Sunnyvale; Masaaki Adachi, Palo Alto, both of Calif.

[73] Assignee: Catalytica, Inc., Mountain View, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 08/715,588

[22] Filed: Sep. 18, 1996

[51] Int. Cl.[6] ............................... C07C 5/22; C07C 4/12; B01J 29/18; C10G 35/06

[52] U.S. Cl. .......................... 585/475; 585/475; 585/489; 502/339; 502/78; 208/138

[58] Field of Search ..................... 585/470, 474, 585/475, 489; 502/339, 78; 208/138

[56] References Cited

U.S. PATENT DOCUMENTS

| 3,476,821 | 11/1969 | Brandenburg et al. | 260/672 |
|---|---|---|---|
| 3,480,539 | 11/1969 | Voorhies et al. | 208/111 |
| 3,562,345 | 2/1971 | Mitsche | 260/672 |
| 3,671,602 | 6/1972 | Inoue et al. | 585/475 |
| 3,677,973 | 7/1972 | Mitsche et al. | 252/455 Z |
| 4,162,214 | 7/1979 | Maslyansky et al. | 585/471 |
| 4,210,770 | 7/1980 | Marcilly | 585/474 |
| 4,723,048 | 2/1988 | Dufresne et al. | 585/474 |
| 5,336,824 | 8/1994 | Shamshoum et al. | 585/475 |

*Primary Examiner*—Walter D. Griffin
*Assistant Examiner*—Thuan D. Dang
*Attorney, Agent, or Firm*—Al A. Jecminek

[57] ABSTRACT

This invention is an improved process for the conversion of a $C_9$ mixed alkyl aromatic feedstream containing ethyl substituted aromatics to a product rich in toluenes and/or xylenes via catalytic transalkylation/disproportionation using a palladium loaded moderately, dealuminated mordenite catalyst in the presence of added hydrogen and benzene.

11 Claims, No Drawings

SELECTIVE CATALYTIC CONVERSION OF A C$_9$ AROMATIC FEEDSTOCK CONTAINING SUBSTANTIAL AMOUNTS OF ETHYL SUBSTITUTED AROMATIC COMPONENTS TO A PRODUCT RICH IN TOLUENE AND/OR XYLENES

FIELD OF THE INVENTION

This invention relates to an improved process for the conversion of a C$_9$ mixed alkyl aromatic feedstream containing ethyl substituted aromatics to a product rich in toluene and/or xylenes via catalytic transalkylation/disproportionation. More particularly, this invention is directed to the production of toluene and/or xylenes by transalkylation of benzene with a C$_9$ aromatic feedstock containing substantial amounts of ring ethyl groups using a metal loaded mordenite catalyst which selectively de-ethylates the aromatic ring without causing loss of aromaticity or ring methyl groups under transalkylation reaction conditions.

BACKGROUND OF THE INVENTION

The transalkylation and disproportionation of alkyl aromatics to produce specific single ring aromatic products of high value is an important process in the petroleum refining and petrochemical industry. Disproportionation and transalkylation are well-known reactions which allow exchange of alkyl groups between two aromatic ring compounds. Such reactions typically involve the exchange of ring methyl groups, for example, the disproportionation of toluene to produce benzene and xylenes, or the transalkylation reaction between toluene and trimethylbenzene to produce xylenes. In this regard, it is highly desirable to carry out the reactions with no yield loss of aromatic rings and with retention of the desired methyl groups. For toluene disproportionation, which produces products primarily in the C$_6$ to C$_8$ range, certain catalysts can be utilized (such as ZSM-5 zeolite) without the use of a metal co-catalyst or added hydrogen. For transalkylation reactions involving aromatic molecules in the range C$_9$ and higher, zeolites, having a larger pore structure than zeolite ZSM-5, are utilized and it is generally necessary to add a metal co-catalyst and operate with a co-feed of hydrogen in order to retard catalyst deactivation and to maintain an acceptable catalyst life.

Recently, there has been increasing interest in developing methods to reduce the benzene content in gasoline. As a result, there is interest in carrying out transalkylation reactions of alkyl-substituted aromatics with benzene, especially reactions of C$_9$ and (optionally, C$_{10}$) aromatic feedstocks, to produce valuable xylene and toluene. Even more desirable, would be a process which could produce high yields of xylene and toluene products using feedstocks containing high proportions of C$_9$ components, including even 100 percent C$_9$-based feedstocks. Transalkylation of such C$_9$-rich feedstocks has, until now, been uneconomic due to the rapid deactivation of catalysts when feeds predominantly comprising C$_9$ aromatics are used. It is believed that this is in large measure due to the concentration of ethyl and higher alkyl side chain groups on the aromatic ring, specifically, the ethyl toluene components in the C$_9$ feed. These groups are much more likely to participate in condensation reactions leading to polynuclear aromatic structures which are coke precursors. In addition, transalkylation of C$_9$ feedstocks has typically resulted in substantial levels of C$_{10}^+$ co-products along with the desired xylenes. It is highly advantageous to produce substantial quantities of xylene and toluene from high C$_9$-content feedstocks while maintaining the concentration of undesired C$_{10}^+$ products at a low level. The process of the present invention employing a moderately dealuminated, palladium-loaded mordenite catalyst is designed to meet this requirement.

While the use of palladium-loaded mordenite catalysts, in a variety of hydrocarbon processing reactions including transalkylation, is known in the art, there has been no suggestion or teaching of the application of a moderately dealuminated, palladium-loaded mordenite catalyst to selectively hydrodealkylate ethyl and higher alkyl groups from an aromatic ring under transalkylation reaction conditions, such as is contemplated by the present invention. For example, U.S. Pat. No. 4,489,216, assigned to Lewis, describes a catalyst for isomerization of alkenes and also disproportionation and transalkylation of aromatics. This patent describes use of a mordenite having Si/Al atomic ratio of 5–10, loaded with palladium to a level typically two weight percent. The key aspect of this disclosure is a preferential calcination of this catalyst at temperatures of 1,200–1,500 F., prior to use, to substantially remove Bronsted acid sites and maximize Lewis acid sites. This treatment is claimed to be important for alkene isomerization activity; and there is no discussion of the effect, if any, of the calcination on transalkylation activity of the catalyst much less its effect on activity of the catalyst in the hydrodealkylation of ethyl groups in C$_9$ aromatic feedstocks under transalkylation reaction conditions. Further, the effect of moderate dealumination of the mordenite on the performance of the catalyst in transalkylation of C$_9$ aromatic feeds containing high amounts of ethyl being substituents is clearly not disclosed.

A patent assigned to Novansky and Judec (Czechoslovak Patent No. CS 235566) describes a catalyst comprising 40% mordenite, 60% alumina and 0.5% palladium for the transalkylation of methylbenzenes, hydrodealkylation of higher alkylbenzenes, and hydro-cracking of non-aromatics. Although this patent describes the potential for hydrodealkylating higher aromatic compounds, for example, hydrodealkylation of ethyl toluene to produce toluene, which can then react with trimethylbenzenes to produce xylenes; there appears to be no recognition regarding the importance of preparing a moderately dealuminated mordenite prior to loading the palladium metal into the zeolite. Attempts to prepare and test the catalyst of this patent have not produced a catalyst which is sufficiently active, selective and stable in the hydrodealkylation of ethyl groups in C$_9$ aromatic feedstocks to be of practical interest. Indeed, in the patent itself, there is no discussion of long-term catalyst performance in any of the patent examples.

Finally, a paper by Bawa et. al. (Erdol und Kohle, Erdgas, Petrochem, 1993, 46[1]:11) describes the use of a catalyst comprising 0.1% Pd on H mordenite for the transalkylation of toluene with trimethylbenzenes. However, there is no discussion of transalkylation of toluene with commercial C$_9$ feedstocks, which include ethyltoluenes, and therefore; no recognition of the importance of hydrodeethylation in such transalkylation reactions. There is also no discussion of the importance of moderate dealumination in improving the performance of the catalyst for transalkylation reactions.

Accordingly, it would be of significant benefit to the art if a catalytic transalkylation process could be developed which would afford high yields of toluene and/or xylenes in a stable operation (minimal coking and deactivation of catalyst) with concomitant low hydrogen consumption, while allowing the use of aromatic feedstocks which contain high amounts of C$_9$ aromatic feed components that are ring substituted with ethyl or higher alkyl groups. With such a process, the range of aromatic feed materials used to produce higher value toluene and/or xylenes could be substantially broadened beyond that heretofore possible.

SUMMARY OF THE INVENTION

It has now been found that moderately dealuminated, palladium-loaded mordenite catalysts, when employed in the transalkylation/disproportionation of a mixed alkyl aromatic feedstock containing benzene and substantial amounts of $C_9$ ethyl and higher alkyl substituted aromatics as well as methyl substituted components, are highly selective in the hydrodealkylation of ethyl and higher alkyl groups from the aromatic ring without causing loss of aromaticity in the feedstock or loss of valuable methyl groups. These moderately dealuminated mordenite catalysts, with Si/Al ratios in the range of about 12 to 30, afford high yields of toluene and/or xylenes in the transalkylation of a mixed alkyl aromatic feedstock containing 20 percent by weight or more $C_9$ aromatics having ring substituted ethyl groups. Because of the unique selectivity which these catalysts exhibit for hydrodealkylation of ethyl and higher alkyl groups, as compared to cleavage of ring methyl substituents and/or hydrogenolysis of aromatic structures, consumption of expensive hydrogen is minimized in the process. Further, the highly active and selective nature of the moderately, dealuminated, Pd-loaded mordenite catalyst towards hydrodealkylation of ring-substituted ethyl groups, coupled with apparent activity in the hydrogenation of coke precursors, affords catalyst lifetimes which are extended relative to other metal-loaded mordenite catalysts.

Accordingly, this invention is a process for the conversion of a mixed aromatic hydrocarbon starting material, containing at least about 20 mole percent of $C_9$ aromatic compounds which are ring substituted with ethyl or higher alkyl groups, into an aromatic hydrocarbon product, which is enriched in toluene and/or xylenes content relative to the starting material and reduced in $C_9$ aromatic content relative to the starting material, which comprises contacting in a reaction zone, the starting material with a catalytically-effective amount of a catalyst comprising palladium on a dealuminated mordenite having a Si/Al ratio of about 12 to 30 in the presence of hydrogen and under temperature and pressure conditions to effect the conversion of said starting material to the product and recovering the product from the reaction zone. In an alternative aspect of the invention, the mixed aromatic hydrocarbon starting material which is used has a benzene content of greater than about 50 percent by weight (58.6 mole %) and the catalytic hydrocarbon conversion is carried out to selectively afford a product high in toluene content. Finally, the process of this invention also contemplates the use of the moderately dealuminated Pd-loaded mordenite catalysts with an added non-acidic e.g., silica, binder. The use of a silica binder provides a catalyst with enhanced handling characteristics without diminishing its activity and selectivity in the hydrocarbon conversion reaction of the invention.

DESCRIPTION OF THE INVENTION

This invention is based, in part, on the finding that a transalkylation/disproportionation catalyst can be derived, with proper choice of catalytic metal, zeolite support and zeolite/metal combinations, which is highly selective in the hydrodealkylation of ethyl and higher alkyl groups from the aromatic ring without loss of aromatic ring or loss of valuable ring methyl groups. Selective hydrodealkylation implies cleavage of ethyl groups from the ring to produce ethane, with simultaneously low methane formation which can occur either via cleavage of methyl groups from the aromatic ring or via hydrogenolysis of the cleaved ethyl group. In accordance with the invention, the metal most selective for this function is palladium, which is added to the mordenite zeolite to form a catalyst containing both acidic and metal functions. The type and nature of the mordenite zeolite is also critical to obtaining the highly selective hydrodealkylation activity which characterizes the process of the invention. In this regard, it has been found that there is an optimal range of Si/Al ratios for best functioning of the mordenite zeolite according to this invention. Since increasing the Si/Al ratio in the zeolite results in a decreasing number of acid sites and, hence, decreasing overall catalyst activity, care must be taken not to excessively dealuminate the zeolite. On the other hand, some level of dealumination of the mordenite leads to favorable performance both in terms of catalyst selectivity and life. In accordance with the invention, it has been found that Si/Al ratio in the range of 12 to 30 provides the most optimal results with dealuminated mordenites having Si/Al ratios of 15–25 being preferred. Most preferably, the above Si/Al ratios include essentially no extra framework aluminum, it being removed in the preparation of the dealuminated mordenite (see below).

The catalytic metal or metal function is essential for the maintenance of catalyst life in the presence of hydrogen while simultaneously providing for high hydrodeethylation activity without hydrogenolysis of the dealkylated fragments to methane, loss of aromatic ring structures, or loss of ring methyl groups. According to the invention, palladium, most notably and unexpectedly, is uniquely effective in accomplishing these simultaneous tasks. Other metals such as Pt, Rh, Ru, Ni, Re, etc. are less effective, especially in terms of the being less selective in hydrodealkylation and generally having undesirable and excessive hydrogenolysis activity. Suitably, the Pd is employed at a concentration of from about 0.3 to about 2.0 weight percent relative to the weight of mordenite in the process of the invention with Pd loadings of about one percent being preferred as most optimal in affording a long-term catalyst life without excessive use of expensive metal. However, the absolute amount of Pd metal added to the zeolite depends to some extent on the processing conditions such as temperature, hydrogen pressure, hydrogen/hydrocarbon ratio in the feed, and space velocity. In general it has been found that low loadings of Pd, less than approximately 0.25 weight percent are insufficient for maintenance of catalyst activity and hydrodealkylation activity under commercially important operating conditions.

In another preferred embodiment of the invention the moderately dealuminated, Pd-loaded mordenite catalyst is combined with a non-acidic binder such as silica or zirconia to enhance the crush strength and other handling characteristics of the catalyst. In this regard, the use of a silica binder is particularly advantageous and preferred in that, in contrast to other common binders such as alumina, the silica binder does not adversely effect catalytic activities or the long-term stability of the catalyst in the transalkylation/ disproportionation reaction. The amount or proportion of a silica binder employed is suitably between about 10 to about 50 percent by weight of the finished catalyst (Pd-loaded mordenite plus silica binder) and, preferably, between about 25 to 35 percent of the finished catalyst. Optimum results in the process of the invention are obtained when the silica binder content is about 30 percent and that binder concentration is most preferred from a catalyst performance standpoint.

Catalyst Preparation

The mordenite zeolite component of the catalyst can be prepared by any conventional technique for the production of a dealuminated mordenite provided care is taken to control the extent of dealumination within the Si/Al ratios which are critical to the present invention (Si/Al ratios of about 12 to 30). Most suitably, and preferably, the dealumination is carried out by the sequential steps of steaming at elevated temperatures followed by acid washing of the steamed mordenite.

In the steaming step, aluminum is removed from the framework but is retained within the solid, forming what is referred to as extra-framework aluminum. The acidity associated with the zeolite is related to the amount of aluminum retained in the structure in a tetrahedrally-coordinated environment. The extra-framework aluminum may be present in sufficient concentration to, in some cases, restrict access to the acid sites within the pore structure of the mordenite, or it may contribute additional and different acidity that is undesirable or difficult to reproduce. The purpose of the subsequent acid wash to dissolve and remove these extra-framework Al species. The final dealuminated zeolite contains an open pore structure and essentially no occluded pores. By creating this more open, porous network, the catalyst has an extended life relative to the non-dealuminated zeolite.

The Si/Al atomic ratio of the commercially available starting mordenite which is to be subsequently dealuminated may vary from about 6/1 to 10/1. A suitable commercial source of mordenite which has been subsequently dealuminated (and utilized in the examples below) is 640HOA mordenite available from Tosoh Corporation. This material consists of exchangeable cations being in the acid ($H^+$) form and has a Si/Al ratio of about 9. In a typical dealumination procedure, a quantity of the mordenite powder is packed into a quartz tube containing a frit to retain the powder and this tube is placed into a split tube furnace heated by electrical resistance. Air is passed upflow through the packed tube and the zeolite powder is heated in flowing air about 150° C. for two hours, followed by about 400° C. for about two hours. The zeolite is then exposed to a steaming procedure consisting of saturating the flowing air stream with water vapor and passing this stream at about 400° C. for about 10 minutes over the zeolite. It has been found that the time of exposure for this step is not critical, although the process is sensitive to the steam content of the carrier gas. Following this steaming procedure, the steamed mordenite is then added to a solution of nitric acid, typically 0.5 to 1.0 molar, and stirred continuously for approximately two hours. Again, the time of acid washing is not critical, but preferably it is sufficient to remove all extra framework from within the zeolite channels. Some additional removal of tetrahedrally coordinated Al from the mordenite framework may also be accomplished during this acid washing step; however, the primary effect is to remove extra-framework aluminum. The removal of extra-framework aluminum is an important and preferred aspect of this invention. The criterion for acceptable removal of extra-framework Al is based on $^{27}Al$ solid-state NMR analysis, which shows the absence of significant levels of octahedral (non-framework) aluminum remaining within the zeolite. The acid treated material is filtered and washed with distilled water to neutral pH. This dealuminated mordenite most preferably has a final Si/Al ratio of approximately 16 as analyzed by Inductively Coupled Plasma (ICP) analysis and is characterized by substantially all the aluminum ions being tetrahedrally coordinated in the zeolite framework. If it is desired to reduce the Si/Al ratio below 16, say to about 12, this can be accomplished by a reduction in the steam content of the vapor passed over the mordenite during the streaming process. If it is desired to increase the Si/Al ratio to greater than 16, say to 30, this may be accomplished through the use of higher concentrations of nitric acid during the washing step, to approximate 2–3 molar.

The palladium is most effectively introduced into the dealuminated zeolite, via ion exchange procedure although other conventional metal deposition techniques including impregnation methods are also suitable. The mordenite subject to the Pd loading via ion exchange is typically in the protonated or (Bronsted) acid form, a natural consequence of the steaming and acid washing treatment. The dealuminated mordenite may contain other exchangeable cations, such as $Na^+$ or $NH_4^+$ or other metal cations without significantly affecting the course of the ion exchange procedures with Pd. However, the final zeolite is preferably predominately in the Bronsted acid form for maximum effectiveness for transalkylation activity. This zeolite is contacted with an aqueous solution of a suitable Pd salt, e.g., a 0.001 M solution of $Pd(NH_3)_4(NO_3)_2$ in an amount sufficient to afford the desired metal loading, for example, a one percent loading of Pd in the mordenite assuming that full exchange is achieved. In this regard, it has been found that with the high affinity of the Pd cations for the mordenite exchange sites, a single exchange is typically sufficient to incorporate essentially all the available Pd into the zeolite. The resulting slurry comprising the dealuminated mordenite and Pd solution is then heated to about 95 C. for about four hours to complete the exchange. If desired, the exchange may be carried out at lower temperatures including as low a temperature as ambient, but with longer exchange times required to assure complete exchange of the Pd cations into the framework. Following the exchange, the Pd/dealuminated mordenite is filtered, washed with distilled or de-ionized water to neutral pH, and dried in an oven at about 100 C. for 12 to 24 hours. After drying the metal loading in the zeolite should be confirmed by analysis, e.g., by ICP analysis.

Prior to use in the hydrocarbon conversion process of the invention, the mordenite loaded with the palladium salt is subject to a calcination step to oxidize and remove the Pd salt counter ions, e.g., in the case of Pd $(NH_3)_4(NO_3)_2$ the ammine ligands, attached to the Pd cation. The temperature employed in the calcination should be sufficient to effect the oxidation and counter ion removal in an efficient manner but not so high as to remove Bronsted acid sites and create Lewis acid sites in the zeolite matrix. In this regard, calcination temperatures in excess of about 500° C. should be avoided with temperatures in the range of about 340 to 500° C. being most suitable. The calcination is typically carried out by passing a flowing oxygen-containing or a non-reducing gas, e.g., air through the Pd salt-loaded zeolite at the desired calcination temperature for a period of about two to six hours.

As pointed out previously, an alternative and preferred embodiment of the invention involves the use of the moderately dealuminated, Pd-loaded mordenite composited or combined with a silica binder to provide enhanced crush strength handling characteristics. A very suitable procedure for preparing a catalyst according to the invention containing the silica binder using a moderately dealuminated mordenite prepared as described above involves the following sequence of steps:

(a) The dealuminated mordenite is subject to a preliminary calcination to remove water and impurities, such as residual acid used in the dealuminating procedure from the mordenite starting material. This preliminary calcination is suitably carried out in a rotary kiln, under an atmosphere of air with GHSV 100 hr.$^{-1}$ using a step-wise temperature profile where the mordenite is initially heated to about 150° C. and held for about two hours and then heated up to about 500° C. and held for an additional two to four hours.

(b) The precalcined mordenite (after cooling) is then combined with a silica binder and water, and subject to mixing or mulling such that the silica binder is intimately mixed with the mordenite to form an extrudable material. For this step, the silica binder can be previously prepared by mixing a silica sol, e.g., ST-40 from Nissen Chemical, and silicic acid such as that available from Wako Pure Chemical. Here the amount of silica used should be sufficient to afford the desired silica/mordenites ratio in the final catalyst product, e.g., 10–50 percent weight silica in the final catalyst.

(c) The silica/mordenite composite mixture is extruded, e.g., with a 0.8 mm diameter extruder and immediately dried at about 120° C. for about three hours at which time the dried extruded material is cut into the appropriate lengths and sieved, e.g., through a 355–1,000 μm sieve.

(d) The sieved extrudate is then calcined, e.g., in a rotary kiln, under an atmosphere of air with GHSV 200 hr.$^{-1}$ in a step-wise procedure where it is first heated to 150° C. and held for 1.5 hours and then slowly heated to 550° C. and held for about 6.5 hours.

(e) After cooling, the calcined extrudate is subject to ammonium ion exchange by contacting it with a concentrated aqueous ammonium solution at an ambient temperature (about 25° C.) for about four hours after which the extrudate is filtered and dried at about 120° C. for about 12 hours under an atmosphere of an inert gas such as argon or nitrogen.

(f) The ammonium-form of the extrudate is then contacted with an aqueous solution of a Pd salt, e.g., 0.001M Pd $(NH_3)_4(NO_3)_2$ under ion exchange conditions for about 40–48 hours at room temperature to load the zeolite with its desired amount of Pd (in salt form) after which the extrudate is recovered by filtration and dried for about one hour under reduced pressure followed by further drying at about 25° C. for 12–24 hours.

(g) The Pd exchanged extrudate is then calcined under an air atmosphere in a step-wise-fashion whereby the temperature is raised to 150° C. and held at 150° C. for two hours followed by increase to 500° C. where it is held for an additional 2.5 hours.

With this step-wise procedure for preparing catalysts useful in the process of the invention, which procedure constitutes another aspect of the invention, it is possible to prepare catalysts having high crush strengths and rugged-handling properties which exhibit the selective deethylation activity and excellent transalkylation activity characteristic of catalysts used in the process of the invention.

Aromatic Hydrocarbon Starting Material

The aromatic hydrocarbon starting material or reactant source for the process of the invention can be any mixed aromatic feedstock conventionally available in a refinery or chemical plant which is predominately made up of monocyclic $C_6$ to $C_{12}$ aromatic hydrocarbons and contains at least about 20 mole percent of $C_9$ aromatic compounds which are ring substituted with ethyl or higher alkyl groups, e.g., n-propyl or isopropyl. Preferably, the aromatic hydrocarbon starting material contains at least 20 mole percent of $C_9$ aromatic compounds having ethyl ring substituents with feedstocks containing from about 20 to about 50 mole percent ethyl toluene being most preferred. The remainder of the mixed aromatic feedstock can be comprised of a variety of aromatic components including toluene and xylene (usually present in minor amounts) benzene, ethylbenzene and trimethylbenzenes. $C_9$ aromatic compounds having ethyl or higher alkyl ring substituents include ethyl toluene and isopropyl and n-propylbenzenes. In addition the aromatic feedstock can contain minor amounts of $C_{10+}$ aromatic hydrocarbons including diisopropylbenzenes, tetramethylbenzenes, diethylbenzenes, propylbutylbenzenes, triethylbenzenes and tri-n-propylbenzenes. A very suitable aromatic hydrocarbon feedstock for the process of the invention is that typically obtained from distillation of catalytic reformer product including the distillation cut having the composition set forth in Table 1 below which was utilized in a number of the experimental examples subsequently set forth below. In addition to ethyltoluenes, the feedstock has significant quantities of n-propyl and isopropyl benzenes.

TABLE 1

Composition of Commercial C9 Feedstock

| Feed Component | Mole % in Feed |
| --- | --- |
| Xylenes | 0.19 |
| Ethyltoluenes | 33.16 |
| Trimethylbenzenes | 56.36 |
| Propylbenzenes | 6.13 |
| C10+ aromatics | 3.42 |
| Saturated hydrocarbons | 0.02 |
| Unidentified | 0.72 |

To optimize the proportion of desired toluene and/or xylenes in the reactor product of the process of the invention, it is desirable to employ aromatic feedstocks in which the concentration of benzene can be varied. The concentration of benzene in the feed is selected so that the overall ratio of methyl substituents to aromatic rings is the same as the desired product; i.e., for maximum production of toluene, the feed component ratios should be selected so that the total number of available substituent methyl groups is equal to the total number of single aromatic rings; for maximal production of xylenes, the ratio of available methyl groups to aromatic rings should be 2:1. Therefore, in a preferred aspect of the invention, the production of toluene using a $C_9$ feedstock such as defined above is optimized by using at least 50 mole percent benzene with benzene contents in the range of about 50 to about 85 mole percent being preferred. With this same $C_9$ feedstock, in order to maximize xylene production, a feedstock containing only 10–15 mole % benzene would be preferred. On the other hand, with a $C_9$ feedstock source containing only trimethylbenzenes, toluene production would be maximized using a feedstock comprising 67 mole % benzene, and xylene production would be maximized using a feedstock containing 33 mole % benzene.

The Transalkylation/Disproportionation Process

The aromatic hydrocarbon conversion reaction of the invention can be carried out in any conventional fashion whereby the aromatic hydrocarbon starting material is contacted with the Pd-loaded, moderately dealuminated mordenite catalyst under transalkylation/disproportionation reaction conditions to yield a product which is enriched in toluene and/or xylenes content relative to the starting material. Both batch-wise and continuous reaction procedures may be employed in reactor configurations which are conventionally used with such procedures. Preferably, the reaction is carried out continuously using a fixed-bed, slurry-bed or fluidized-bed reactor configuration. In one specific embodiment of the invention, the Pd-loaded, moderately dealuminated catalyst is placed in a fixed bed in a reaction zone of a vertical tubular reactor and the mixed aromatic hydrocarbon feedstock plus added hydrogen is passed, in intimate admixture, in an upflow or downflow manner through the reaction zone. The contacting of the feedstock and catalyst in the reaction zone may occur at any temperature and pressure which will selectively dealkylate ethyl and higher alkyl-ring substituents while simultaneously effecting transalkylation and/or disproportionation of the remaining and resulting aromatic components to afford a product enriched in toluene and/or xylenes. Typically, the feedstock, in liquid or vapor phase, is contacted with the catalyst in the reaction zone at a temperature in the range of about 340° C. to about 460° C. with temperatures in the range of 375° C. to 425° C. being preferred.

The pressure employed in the reaction zone may vary over wide limits depending on the composition of the aromatic hydrocarbon feedstock, the reaction temperature and whether liquid or vapor phase contacting is desired. Suitably, the reaction zone pressure is in the range of about 100 psig to about 1000 psig with pressures of from 250 psig to 750 psig being preferred. This pressure is imposed substantially by the presence of hydrogen which is added to the reactant feed to provide about 1 to about 6 moles of hydrogen per mole of hydrocarbon. This amount of hydrogen serves to stabilize the catalyst function as well as at as a source of reactant in the deethylation reaction. In a preferred aspect of the invention any unreacted hydrogen is recovered from the reaction product and recycled to the reaction thus reducing any hydrogen consumption.

The process of the invention can be effected over a wide range of reactant space velocities when carried out on a continuous fashion using the preferred fixed bed reactor. The space velocity selected will depend on a variety of factors, including the feedstock/catalyst ratio, reaction temperature, reaction pressure and the reactor and catalyst-bed design selected. In general, in a continuous fixed-bed reaction process, the weight hourly space velocity (WHSV), i.e., weight of reactant per weight of catalyst per hour, is held at between about 1 and about 10 with WHSV in the range of 2 to 6 being preferred.

Upon completion of the reaction, the product enriched in toluene and /or xylenes can be recovered, for example, by fractional distillation from hydrogen and undesired heavy ends, if any, and various components in the recovered product can be further isolated using conventional separation methodology. The catalyst itself may be added to the reaction zone in any conventional form used in the art for particulate or heterogeneous catalysts. Suitably, the catalyst may be in the form of granules, e.g., 10 to 60 mesh Tyler Standard Screen Scale, or the catalyst may be added in the form of pellets, rings, tablets or extrusions, such as those formed when a silica binder is employed. After the catalyst is loaded into the reaction zone it is suitably treated with hydrogen at elevated temperatures to ensure all the palladium metal presents in the reduced or metallic form. Typically, this hydrogen treatment is carried out by passing hydrogen over the catalyst (GHSV of 1000 to 5000) at a temperature of from about 350° C. to about 500° C. for a period of time ranging from about 1 to about 10 hours. Preferably, the catalyst is treated with hydrogen at 375° C. to 450° C. for 2–5 hours, prior to introduction of the aromatic hydrocarbon feedstock.

In a typical operation of the process of the invention, it is possible to achieve yields to toluene and xylenes in excess of 40 and 20 percent, respectively with ethyl toluene conversion in the range of about 90 to about 95 percent while retaining over 95 percent of the aromaticity originally present in the reactant feed. Further, the retention of ring methyl groups is quite high (losses below five percent) and the catalyst exhibits stable operation beyond that which is obtained with other metal-loaded mordenite catalysts.

Several specific examples of experimental methods for the transalkylation of a mixed aromatic feed rich in $C_9$ aromatics having ring ethyl substituents both according to the invention and comparative examples using catalysts and conditions not according to the invention are described below.

General Procedures

A. Feedstock Source and Composition

The $C_9$ aromatic hydrocarbon reactant employed in most of the following examples has the composition given in Table 1 above. This feed composition is typical of that derived from fractional distillation of a catalytic reformer product, being the cut which boils above approximately 150° C. To simulate normal transalkylation conditions in a number of examples, this $C_9$ feed was mixed with added benzene in a benzene to $C_9$ aromatic ratio of 1:2 by weight. In certain examples to test catalyst deactivation under stressing conditions the $C_9$ feedstock without added benzene was used. Further, in other examples to evaluate the process of the invention in producing a toluene product in high selectivity a range of benzene contents of from about 30% by weight to about 85% by weight were employed in addition to the $C_9$ aromatic feed.

B. Catalyst Preparation

The mordenite zeolite employed in the examples as a catalyst component was 640HOA mordenite, available from Tosoh Corporation, having exchangeable cations in the acid ($H^+$) form and being in the non-dealuminated (Si/Al ratio of about 9) form. In examples, according to the invention, the 640HOA mordenite was subject to dealumination using the following procedure: approximately 100 g of the 640HOA mordenite powder is packed into a 1 inch i.d. quartz tube containing a frit to retain the powder and this tube is placed into a split tube furnace heated by electrical resistance. Air is passed upflow through the packed tube at a flow rate of 100 cc/minute. The zeolite powder is heated in flowing air at 150 C. for two hours; followed by 400° C. for one hour. The zeolite is then exposed to a steaming procedure consisting of saturating the flowing air stream with water vapor and passing this stream at 400° C. for 10 minutes over the zeolite. Following this steaming procedure, the steamed mordenite is then added to a solution of nitric acid (0.5 to 1.0 molar), and stirred continuously for approximately two hours at a temperature of 95° C.

The palladium metal was then deposited on the mordenite either dealuminated, as describe above, or non-dealuminated (for comparative example purposes) using the following procedure: a 0.001M solution of Pd $(NH_3)_4(NO_3)_2$ was prepared by dissolving the Pd salt in distilled water and 400–1600 ml of the 0.001M Pd solution, dependent on the Si/Al ratio of the mordenite, was added to 10 grams of them mordenite in a beaker equipped with a magnetic stirring bar. The resulting slurry of mordenite in the 0.001M Pd solution is then heated to 95° C. for about four hours to complete the impregnation of the mordenite with the Pd salt by ion exchange. Following the exchange, the Pd/mordenite is filtered, washed with distilled or de-ionized water to neutral pH, and dried in an oven at 100° C. overnight. ICP analysis has verified that the metal loading in the zeolite is approximately one percent by weight. Other Pd metal loadings on the mordenite were accomplished using the same procedure described above and using the same concentration of Pd salt in the aqueous solution, but adjusting the total amount of solution to provide the required amount of Pd.

For the majority of the experiments, the Pd/mordenite catalyst is evaluated for transalkylation in the absence of a binder or other additives. A subsequent example will describe the preparation of the catalyst with, preferentially, a silica binder. The Pd/mordenite powder is first ground in a mortar and pestle and the ground powder is placed in a die and pressurized to produce a flat tablet. This tablet is then broken up to produce a granular material having mesh size 40–60 (Tyler). At this point, the catalyst is subjected to a calcination step to oxidize the remove the ammine ligands attached to the Pd cation. This step may be done external to the catalytic reactor or may be carried out in situ. The calcination is typically carried out at 340–500° C. with flowing air at a space velocity (GHSV) of 100–200 for 2–6 hours. The catalyst, if not already in the catalytic reactor, is now loaded into the reactor and is then subjected to a reduction step in flowing hydrogen (GHSV=3000–6000) for 2–6 hours at 400° C.

C. Reaction Procedures

The primary components of the test reactor include: a piston pump for accurate delivery of the aromatic feedstock to the reactor, and mass flow controllers for delivery of gaseous reagents such as hydrogen; a tubular fixed bed reactor, i.d. ½", capacity up to 5 grams of catalyst; a split tube furnace to heat the catalyst bed; a back pressure regulator, and on-line gas chromatographic detection of products. Typically 1–2 grams of calcined catalyst is loaded into the reactor, following which glass beads are loaded above the catalyst bed to provide a preheating section to assure the liquid feed is vaporized prior to reaching the catalyst. The aromatic feedstock plus hydrogen are passed down-flowing through the catalyst bed. Prior to the onset of catalyst testing, the catalyst is pretreated in flowing hydrogen (75–200 sccm) for two hours at 400° C. Following this pretreatment, which results in reduction of the palladium species, the hydrogen flow is adjusted and the aromatic feedstock is allowed to flow over the catalyst. Although conditions and procedures vary depending on the particular experiment, typical operating conditions for many experiments used for comparison of catalyst performance are:

reaction temperature: 400° C.
catalyst charge: 2 g
feedstock: 1 part benzene/2 parts $C_9$ aromatic feedstock (defined above) by weight
aromatic reactant flow: 3 WHSV (weight hourly space velocity)
hydrogen/hydrocarbon mole ratio: 3
reactant pressure: 290 psig
reaction duration: 6–16 hours, except in the case of extended life tests The products of the reaction are measured via on-line GC analysis, typically every 2 hours, allowing the progress of reaction to be monitored as well as any possible catalyst deactivation. The aromatic reaction products through $C_{10}$, which have been identified by retention time by authentic standards, are measured individually, as are all saturated components in the $C_1$–$C_6$ range. Aromatic product above $C_9$ ($C_{10}^+$) is lumped together for the analysis report, although products can be separated into $C_{10}$, $C_{11}$, and $C_{12}$ components since the analysis separates the product primarily by boiling point. All products are converted from a weight basis to a mole basis for the subsequent analysis.

It has been found that under the above reaction conditions, a good catalyst typically maintains good performance over the course of the 16 hour test, with the important aromatic components (xylene, toluene) being present at essentially equilibrium concentrations. In order to further delineate differences in performance with such catalysts, it was necessary to go to more extreme reaction conditions to force the performance into a kinetic rather than thermodynamic regime. In this case, a feedstock comprising 100% $C_9$ (no benzene) was utilized and the reaction was carried out under the following conditions:

catalyst charge: 1 g
reaction temperature: 350° C.
aromatic reactant flow: 12 WHSV
hydrogen/hydrocarbon mole ratio: 3
reactant pressure: 290 psig
reaction duration: 16 hours Progress of reaction is monitored with respect to conversion of the reactants, which are grouped into benzene, trimethylbenzenes, and ethyltoluenes; and yields of key products toluene, xylene, $C_1$–$C_6$ light saturates, and $C_{10}^+$ aromatics.

Conversion of the aromatic feedstock A is defined by:

$$(moles_{A,in} - moles_{A,out})/moles_{A,in}$$

Yield of product B is defined by:

$$moles_{B,out}/moles_{total\ hydrocarbon\ feed,\ in}$$

The light hydrocarbons production determines the effectiveness of the catalyst in selective hydrodealkylation, especially hydrodeethylation. A selective catalyst for purposes of this invention shows high yields of ethane (on a molar basis, the ethane yield may be equivalent to the initial amount of ring ethyl substituents); low methane formation, and moderate production of propane (equivalent to the amount of initial propyl substituents in the aromatic feed). Since it is not possible to determine directly whether the $C_2$ and $C_3$ products are produced by selective hydrodealkylation reaction, the % loss of methyl, ethyl, and total aromatics is also determined. These are defined by:

$$methyl\ group\ loss = (moles_{methyl\ groups,\ in} - moles_{methyl\ groups,\ out})/moles_{methyl\ groups,\ in}$$

Ethyl group loss and total aromatic loss are calculated analogously. For the case of the $C_{11}$ and $C_{12}$ product fractions, the presence of 3 methyl groups on each aromatic product, hence 1 ethyl group for each $C_{11}$ aromatic and 1.5 ethyl groups for each $C_{12}$ product was assumed.

Thus, for example, a catalyst that has high production of ethane and propane but also has significant loss of aromatics is not a candidate catalyst according to this invention, since the formation of the $C_2$ and $C_3$ products may also come from hydrogenolysis and hydrocracking of the aromatic structures, notably benzene. In all cases the formation of methane byproduct is undesirable. Methane may form by hydrogenolysis, either of the ethyl and propyl groups derived via hydrodealkylation, by ring demethylation, or by hydrogenolysis of aromatic rings. Low methane formation (which implies low hydrogenolysis activity) along with the retention of >95% of aromatic ring methyl groups is also a feature of our invention.

Another key aspect of the catalyst performance is catalyst life. In commercial application, long catalyst life is essential for economic catalyst performance. Based on the performance of the catalyst over runs of several hours to several days, it is possible to extrapolate the data and predict the age at which time the catalyst activity will need to be increased, either by raising the reaction temperature or by regenerating the catalyst. In this regard, it is convenient to characterize the catalyst performance in terms of a deactivation parameter, $\alpha$. This parameter may be calculated by fitting the conversion versus time data to the following equation: $C=C_o\exp(-\alpha t)$ where C is the conversion at time t of the reactant, $C_o$ is the initial conversion, and $\alpha$ is the deactivation parameter which can be determined separately for each of the feed components. In a good catalyst, the a parameters for each feed component are comparable and low, preferably below 0.01. In practice, the parameters differ somewhat, since some catalysts consume benzene via hydrogenolysis as well as by transalkylation, and the conversion of ethyltoluene is a combination of conversion by selective deethylation and via transalkylation. But, it is necessary at least for these $\alpha$ parameters to be as low as possible.

EXAMPLE 1

Transalklation Performance of Pd/dealuminated Mordenite Catalyst

This example describes the transalkylation of benzene/$C_9$ feedstock under typical transalkylation conditions with a Pd/dealuminated mordenite catalyst which is part of this invention. The experimental procedures are as described in section C above. The Si/Al atomic ratio of the dealuminated mordenite catalyst, prepared as described above, was 16. The Pd loading, prepared via ion exchange, was 1%. The conditions of the experiment, product distribution, and other relevant information from the experimental run are summarized in Table 2. The product is characterized by high yields of xylene and toluene, low $C_{10}^+$ make, and significant amounts of ethane. The high conversion of ethyltoluenes and the high yield of ethane is related to the ability of the catalyst to selectively hydrodeethylate the ethyltoluene fraction of the feed, resulting in a substantial amount of toluene, which may either appear as product or undergo reaction with trimethylbenzenes (TMB), producing xylenes. The existence of low methane make, low hydrogen consumption, and high aromatic ring retention suggest that hydrogenolysis of either the aromatic rings or the ethane produced by hydrodeethylation does not occur. This is necessary for an economic process which does not consume aromatic rings or excessive levels of hydrogen.

TABLE 2

| | | |
|---|---|---|
| Reaction Temperature, K. | 673 | 673 |
| Reaction Pressure, psig | 290 | 290 |
| WHSV, hr-1 | 3 | 3 |
| H2/hydrocarbon, mol/mol | 3.6 | 3.6 |
| Bz/C9 wt./wt. | 0.5 | 0.5 |
| Time on stream | 2 hours | 16 hours |
| Conversion, % | | |
| Benzene | 53.0 | 46.2 |
| Trimethylbenzenes | 81.9 | 83.2 |
| Ethyltoluenes | 98.1 | 97.5 |
| Product yields, mole % on feed | | |
| Methane | 0.5 | 0.4 |
| Ethane | 23.2 | 19.8 |
| C3 + C4 saturates | 16.0 | 12.9 |
| Toluene | 38.7 | 40.9 |
| Xylenes | 23.8 | 23.6 |

TABLE 2-continued

| | | |
|---|---|---|
| C10+ aromatics | 1.2 | 1.2 |
| Loss of ring methyl groups, % | 5.0 | 4.5 |
| Loss of ring ethyl groups, % | 92.8 | 91.5 |
| Loss of aromatic rings, % | 10.0 | 5.2 |
| Catalyst deactivation parameter $\alpha$ | | |
| Benzene | | 0.0062 |
| Trimethylbenzenes | | 0.0001 |
| Ethyltoluenes | | 0.0005 |

EXAMPLE 2

Demonstration of the Preferred Moderate Level of Dealumination for the Pd/Mordenite Catalyst System for Benzene/$C_9$ Transalkylation The following example compares the performance 1% Pd/mordenite at various Si/Al ratios, i.e. at various levels of dealumination. Five mordenite samples of varying Si/Al ratio were loaded with 1 wt. % Pd via ion exchange and compared in the translkylation of Benzene with $C_9$ feed. The mordenite sample having a Si/Al ratio of 9 (catalyst "A") was obtained from Tosoh Corporation (640HOA) and was used without further treatment of the mordenite. The mordenite sample having a Si/Al ratio of 14.2 (catalyst "B") was prepared by steaming at 400° C. for 60 minutes at a steam concentration 16% of saturation, followed by acid washing with 0.5M $HNO_3$ for 2 hours at 95° C. The mordenite sample having a ratio of 16 (catalyst "C") was prepared as described above, i.e. steaming at 400° C. for 10 minutes at a steam concentration 100% saturated, followed by acid washing with 0.5M $HNO_3$ for 2 hours at 95° C. A mordenite sample having Si/Al ratio of 27.6 (catalyst "M") was prepared by steaming at 400° C. for 10 minutes at a steam concentration 100% saturated, followed by acid washing with 4M $HNO_3$ for 2 hours at 95° C. A mordenite sample having higher Si/Al ratio of 40 (catalyst "E") was obtained by steaming at 400° C. for 10 minutes at a steam concentration 100% saturated, followed by acid washing with 3M HCl for 2 hours at 95° C. The loading of the samples with 1 wt. % Pd by ion exchange, and pretreatment is as described above.

In comparing various mordenite catalysts loaded with the same amount of Pd, it has been found that the differences observed are small in standard tests of duration of 8–16 hours, whereas tests of several days duration show substantial differences in terms of catalyst performance, notably in terms of catalyst deactivation. For this reason, the conditions of the transalkylation test were modified in order to more fully stress the catalyst and more clearly reveal the differences between catalyst formulations. The major difference in the test is that lower reaction temperatures, higher space velocities, and 100% $C_9$ feedstocks are utilized. The comparison of the 1% Pd/mordenite samples under these more stressing conditions are shown in Table 3. The data demonstrate the dear superiority of the moderately dealuminated catalysts B, C, and D (Si/Al ratio 14–28) in terms of catalyst activity and of yield of the desirable products xylene and toluene, whereas mordenite catalysts having Si/Al ratios outside this range show poorer performance.

TABLE 3

| | | | | | |
|---|---|---|---|---|---|
| Reaction Temperature, K. | 623 | 623 | 623 | 623 | 623 |
| Reaction Pressure, psig | 290 | 290 | 290 | 290 | 290 |
| WHSV, hr-1 | 11.8 | 11.8 | 11.8 | 11.8 | 11.8 |
| H2/hydrocarbon, mol/mol | 3 | 3 | 3 | 3 | 3 |
| C9, % in feed | 100 | 100 | 100 | 100 | 100 |
| | Catalyst A | Catalyst B | Catalyst C | Catalyst D | Catalyst E |
| Si/Al atomic ratio | 9 | 14.2 | 16 | 27.6 | 40 |
| Reaction time | 8 hours | 8 hours | 8 hours | 8 hours | 8 hours |
| Conversion, % | | | | | |
| Trimethylbenzenes | 28.3 | 38.7 | 37.8 | 34.7 | 21.6 |
| Ethyltoluenes | 42.6 | 58.5 | 55.6 | 55.8 | 36.6 |
| Product yields, mole % on feed | | | | | |
| C1–C6 saturates | 6.4 | 13.7 | 13.4 | 11.6 | 6.3 |
| Toluene | 7.0 | 11.1 | 11.0 | 10.5 | 7.1 |
| Xylenes | 11.6 | 19.5 | 19.0 | 17.2 | 9.4 |
| C10+ aromatics | 16.2 | 14.7 | 15.0 | 14.6 | 13.0 |
| Loss of aromatic rings, % | 2.6 | 0.7 | 1.0 | 0.9 | 0.5 |

EXAMPLE 3

Comparison with Pd/Mordenite Catalysts Comprising Predominantly Lewis Rather than Bronsted Acidity U.S. Pat. No. 4,489,216, assigned to Lewis (discussed above), describes a catalyst for transalkylation of aromatics, using a mordenite zeolite loaded with palladium. The key teaching is a preferential calcination of this catalyst at temperatures of 1200–1500° F. prior to use to substantially remove Bronsted acid sites and maximize Lewis acid sites. In the present invention it has been found that Bronsted acidity is important for transalkylation, and is readily available on zeolites in the $H^+$ form under conditions typical of our operation. In this example the effect of treating a preferred catalyst formulation of the invention at 1350° F., in order to remove substantially all the Bronsted acid sites and convert them to Lewis acid sites was evaluated. The results of the comparison of benzene/$C_9$ transalkylation with the standard conditions set forth in section C above and pretreatment protocols (described above) are summarized in Table 4. It is clear that the protocols described in the Lewis patent (not according to this invention) result in a catalyst having lower activity, faster rates of deactivation, and lower yields of toluene and xylene.

TABLE 4

| | According to this invention | | Not according to this invention | |
|---|---|---|---|---|
| Reaction Temperature, K. | 673 | | 673 | |
| Reaction Pressure, psig | 290 | | 290 | |
| WHSV, hr-1 | 3 | | 3 | |
| H2/hydrocarbon, mol/mol | 3.6 | | 3.7 | |
| Bz/C9 wt./wt. | 0.5 | | 0.5 | |
| Calcination temperature | 500 C. (932 F.) | | 732 C. (1350 F.) | |
| *Reduction temperature | 400 C. | | 400 C. | |
| | 2 hours | 16 hours | 2 hours | 16 hours |
| Conversion, % | | | | |
| Benzene | 53.0 | 46.2 | 42.4 | 32.4 |
| Trimethylbenzenes | 81.9 | 83.2 | 73.4 | 59.7 |
| Ethyltoluenes | 98.1. | 97.5 | 85.3 | 78.2 |
| Product yields, mole % on feed | | | | |
| Methane | 0.5 | 0.4 | 0.4 | 0.2 |
| Ethane | 23.2 | 19.8 | 10.0 | 6.7 |
| C3 + C4 saturates | 16.0 | 12.9 | 6.5 | 5.1 |
| Toluene | 38.7 | 40.9 | 33.7 | 26.3 |
| Xylenes | 23.8 | 23.6 | 23.5 | 19.6 |
| C10+ aromatics | 1.2 | 1.2 | 2.7 | 3.5 |
| Loss of ring methyl groups, % | 5.0 | 4.5 | 0.0 | 0.0 |
| Loss of ring ethyl groups, % | 92.8 | 91.5 | 61.6 | 43.9 |
| Loss of aromatic rings, % | 10.0 | 5.2 | 1.2 | 0.0 |
| Catalyst deactivation parameter α | | | | |
| Benzene | | 0.0062 | | 0.0188 |
| Trimethylbenzenes | | 0.0001 | | 0.0147 |
| Ethyltoluenes | | 0.0005 | | 0.006 |

EXAMPLE 4

Comparison with Other Patent Art

A patent issued to Novansky et. al. (Czech. Patent No. 235566 B1; 1987), also discussed previously, describes the use of a catalyst comprising 40% mordenite and 60% alumina loaded with 0.5 wt. % Pd for transalkylation, hydrodealkylation, and hydrocracking of aromatics. A catalyst was prepared according to their description using a non-dealuminated mordenite (Si/Al=6) (Norton, 100H), a commercially available gamma alumina (VGL, La Roche) and addition of Pd at 0.5% by impregnation. The pretreatment (calcination and reduction) conditions are the same as utilized in Example 1. Transalkylation of the standard benzene/$C_9$ feed was carried out using the conditions in the patent description. The results are summarized in Table 5. It is dear that the catalyst and conditions utilized in the present invention provide superior results to those produced in the previous art described by Novansky et. al. (not according to this invention), the latter which produce uniformly lower conversion, faster catalyst deactivation, and lower yields of desired toluene and xylene. We believe a major aspect of this to be due to the improved formulation of the moderately dealuminated mordenite.

TABLE 5

|  | Not according to this invention | | According to this invention | |
| --- | --- | --- | --- | --- |
| Reaction Temperature, K. | | 693 | | 673 |
| Reaction Pressure, psig | | 308 | | 290 |
| WHSV, hr-1 | | 5.2 | | 3 |
| H2/hydrocarbon, mol/mol | | 14.7 | | 3.6 |
| Bz/C9 wt./wt. | | 0.5 | | 0.5 |
|  | 2 hours | 16 hours | 2 hours | 16 hours |
| Conversion, % | | | | |
| Benzene | 35.7 | 21.3 | 53.0 | 46.2 |
| Trimethylbenzenes | 62.7 | 37.2 | 81.9 | 83.2 |
| Ethyltoluenes | 90.9 | 76.1 | 98.1 | 97.5 |
| Product yields, mole % on feed | | | | |
| Methane | 0.8 | 0.4 | 0.5 | 0.4 |
| Ethane | 15.0 | 9.4 | 23.2 | 19.8 |
| C3 + C4 saturates | 8.5 | 5.3 | 16.0 | 12.9 |
| Toluene | 31.3 | 20.9 | 38.7 | 40.9 |
| Xylenes | 22.3 | 15.9 | 23.8 | 23.6 |
| C10+ aromatics | 1.8 | 2.7 | 1.2 | 1.2 |
| Loss of ring methyl groups, % | 0.0 | 0.0 | 5.0 | 4.5 |
| Loss of ring ethyl groups, % | 77.5 | 49.1 | 92.8 | 91.5 |
| Loss of aromatic rings, % | 2.3 | 0.3 | 10.0 | 5.2 |

EXAMPLE 5

Comparison with Additional Prior Art

A specific citation in the literature (Bawa et. al.; Erdol und Kohle-Erdgas, *Petrochem;* 1993; 46[1]; 11–13) also described above describes a process for transalkylation of toluene with trimethylbenzenes using a catalyst comprising 0.1% Pd on H mordenite. The process described in that reference was compared to the process of the present invention in order to demonstrate that the present invention is preferred for transalkylation of benzene with commercial feedstocks, especially those containing ethyltoluenes. A catalyst comprising 0.1% Pd/Tosoh mordenite (640HOA) was prepared by ion exchange, following the protocols described above. This catalyst was evaluated for transalkylation of benzene/$C_9$ feedstock using the processing conditions recommended in the Bawa article (not according to the invention). A comparison of these results with the process according to the invention is provided in Table 6. It is clear from this comparative example that the prior art catalyst has poorer performance. The high operating temperature and high $H_2$/hydrocarbon ratio compensates somewhat for the low loading of Pd and the non-optimal Si/Al ratio of the zeolite. However, this results in significant light ends formation and lower yields of the desired products xylene and toluene. Thus, the cited article does not teach the advantages described in the present invention of selective de-ethylation with minimal ring demethylation and low hydrogen consumption.

TABLE 6

|  | 1% Pd/ mordenite According to this invention | | 0.1% Pd/ mordenite Not according to this invention | |
| --- | --- | --- | --- | --- |
| Reaction Temperature, K. | | 673 | | 723 |
| Reaction Pressure, psig | | 290 | | 308 |
| WHSV, hr-1 | | 3 | | 1.3 |
| H2/hydrocarbon, mol/mol | | 3.6 | | 8.5 |
| Bz/C9 wt./wt. | | 0.5 | | 0.5 |
|  | 2 hours | 16 hours | 2 hours | 16 hours |
| Conversion, % | | | | |
| Benzene | 53.0 | 46.2 | 49.7 | 48.6 |
| Trimethylbenzenes | 81.9 | 83.2 | 93.9 | 88.3 |
| Ethyltoluenes | 98.1 | 97.5 | 98.8 | 98.1 |
| Product yields, mole % on feed | | | | |
| Methane | 0.5 | 0.4 | 10.1 | 6.1 |
| Ethane | 23.2 | 19.8 | 68.4 | 39.5 |
| C3 + C4 saturates | 16.0 | 12.9 | 44.9 | 28.5 |
| Toluene | 38.7 | 40.9 | 28.5 | 35.8 |
| Xylenes | 23.8 | 23.6 | 11.8 | 18.5 |
| C10+ aromatics | 1.2 | 1.2 | 0.8 | 1.2 |
| Loss of ring methyl groups, % | 5.0 | 4.5 | 46.6 | 22.8 |
| Loss of ring ethyl groups, % | 92.8 | 91.5 | 97.3 | 91.4 |
| Loss of aromatic rings, % | 10.0 | 5.2 | 34.9 | 18.2 |
| Deactivation parameter, α | | | | |
| Benzene | | 0.0062 | | 0.0014 |
| Trimethylbenzene | | 0.0001 | | 0.0032 |
| Ethyltoluene | | 0.0005 | | 0.0004 |

EXAMPLE 6

Demonstration of the Unique Advantages of Pd Metal in Conjunction with Dealuminated Mordenite for Transalkylation Other noble metals are known for their hydrogenation activity and ability to retard catalyst deactivation by coke formation by hydrogenating coke precursors. However, it has been found, according to this invention, that Pd has the unique property of providing selective hydrodealkylation of the ethyl and higher alkyl side chain groups without simultaneously promoting undesirable side reactions such as loss of aromatic methyl groups or hydrogenolysis of aromatic structures leading to excessive hydrogen consumption and loss of total aromatic product. In this example, 1 wt. % Pt/dealuminated mordenite (Si/Al=16) and 1 wt. % Rh/dealuminated mordenite (Si/Al=16) catalysts were prepared via ion exchange procedures using $Pt(NH_3)_4(NO_3)_2$ and $RhCl_3$, respectively, followed by drying, calcination and reduction using standard conditions described above. These catalysts were evaluated for the transalkylation reaction of benzene/$C_9$ feedstock and compared with 1 wt. % Pd/dealuminated mordenite, as summarized in Table 7. It is clear from the results that Pd provides superior performance with dealuminated mordenite compared to the other noble metals. Notably, the high hydrogenolysis activity of Pt results in significantly higher $C_1$–$C_4$ product, lower toluene yields, and substantial loss of aromatic rings. The very high yield of methane with the 1% Rh case shows that rhodium provides very high hydrogenolysis activity toward both ring alkyl groups and aromatic rings, resulting in unacceptably high aromatics loss and hydrogen consumption. The xylene yields are also lower with the 1% Rh catalysts. The 1% Pd/dealuminated catalyst clearly provides significant advantages compared to the other metals.

100% $C_9$ feed under the more stressing conditions of lower temperature and high space velocity, as described in section C., designed to more significantly differentiate catalyst performance. The results of these comparative evaluations are summarized in Table 8. Under these conditions it is clear that the Pt/mordenite catalyst has significant loss of ring methyl groups and loss of aromatic rings, and the Rh/mordenite

TABLE 7

|  | 1 % Pd/mordenite | | 1 % Pt/mordenite | | 1 %Rh/mordenite | |
| --- | --- | --- | --- | --- | --- | --- |
| Reaction Temperature, K. | 673 | | 673 | | 673 | |
| Reaction Pressure, psig | 290 | | 290 | | 290 | |
| WHSV, hr-1 | 3 | | 3 | | 3 | |
| H2/hydrocarbon, mol/mol | 3.6 | | 3.6 | | 3.6 | |
| Bz/C9 wt./wt. | 0.5 | | 0.5 | | 0.5 | |
| Time on stream | 2 hours | 16 hours | 2 hours | 16 hours | 2 hours | 16 hours |
| Conversion, % | | | | | | |
| Benzene | 53.0 | 46.2 | 81.8 | 77.7 | 58.4 | 57.5 |
| Trimethylbenzenes | 81.9 | 83.2 | 75.8 | 75.5 | 73.8 | 66.6 |
| Ethyltoluenes | 98.1 | 97.5 | 96.8 | 96.3 | 84.9 | 88.4 |
| Product yields, mole % on feed | | | | | | |
| Methane | 0.5 | 0.4 | 14.3 | 23.6 | 176.4 | 169.3 |
| Ethane | 23.2 | 19.8 | 36.0 | 40.0 | 0.0 | 0.0 |
| C3 + saturates | 16.0 | 12.9 | 40.9 | 24.1 | 0.2 | 0.2 |
| Toluene | 38.7 | 40.9 | 23.3 | 26.5 | 24.2 | 21.4 |
| Xylenes | 23.8 | 23.6 | 21.4 | 23.0 | 18.8 | 17.8 |
| C10+ aromatics | 1.2 | 1.2 | 1.7 | 1.9 | 2.2 | 2.6 |
| Loss of ring methyl groups, % | 5.0 | 4.5 | 16.8 | 10.2 | 15.8 | 13.7 |
| Loss of ring ethyl groups, % | 92.8 | 91.5 | 90.3 | 88.8 | 70.5 | 64.4 |
| Loss of aromatic rings, % | 10.0 | 5.2 | 37.8 | 30.8 | 24.9 | 24.2 |

EXAMPLE 7

Comparative Testing of Noble Metal/Dealuminated Mordenite Catalysts Under Conditions Designed to Stress the Catalyst The same catalysts that were evaluated for benzene/$C_9$ transalkylation in Example 6 above were also evaluated with catalyst shows substantial production of methane and heavy aromatics, significant loss of aromatic rings, and decreased selective de-ethylation activity. Only the Pd/mordenite catalyst maintains the ability to selectively de-ethylate the aromatic rings with retention of ring methyl groups and total aromatic content of the product while maintaining low yield of heavy aromatics.

TABLE 8

|  | 1 % Pd/mordenite | | 1 % Pt/mordenite | | 1 % Rh/mordenite | |
| --- | --- | --- | --- | --- | --- | --- |
| Reaction Temperature, K. | 623 | | 623 | | 623 | |
| Reaction Pressure, psig | 290 | | 290 | | 290 | |
| WHSV, hr-1 | 11.8 | | 11.8 | | 11.8 | |
| H2/hydrocarbon, mol/mol | 3 | | 3 | | 3 | |
| C9 content of feedstock, % | 100 | | 100 | | 100 | |
| Time on stream | 2 hours | 8 hours | 2 hours | 8 hours | 2 hours | 8 hours |
| Conversion, % | | | | | | |
| Trimethylbenzenes | 40.4 | 37.8 | 52.4 | 50.2 | 63.3 | 44.6 |
| Ethyltoluenes | 60.1 | 55.6 | 89.9 | 85.6 | 90.0 | 65.4 |
| Product yields, mole % on feed | | | | | | |
| Methane | 0.0 | 0.0 | 1.0 | 0.6 | 6.0 | 57.1 |
| Ethane | 6.9 | 5.6 | 8.7 | 7.5 | 1.0 | 0.2 |
| C3 + C4 saturates | 7.7 | 7.5 | 15.4 | 13.7 | 0.1 | 0.1 |
| Toluene | 11.8 | 11.0 | 4.4 | 4.0 | 5.4 | 5.0 |
| Xylenes | 20.7 | 19.0 | 17.2 | 16.8 | 12.9 | 12.1 |
| C10+ aromatics | 14.6 | 15.0 | 13.6 | 12.3 | 38.6 | 30.9 |
| Loss of ring methyl groups, % | 2.1 | 2.9 | 19.7 | 31.5 | 0.0 | 0.4 |
| Loss of ring ethyl groups, % | 31.8 | 33.9 | 68.7 | 70.6 | 0.0 | 0.0 |
| Loss of aromatic rings, % | 0.8 | 1.0 | 34.7 | 39.0 | 12.7 | 15.3 |

EXAMPLE 8

Performance of Metal/Mordenite Catalysts by Impregnation

The comparative performance in the transalkylation of benzene/$C_9$ feedstock using 1 wt. % Pd/dealuminated mordenite via both ion exchange and impregnation is provided in Table 9. $Pd(NH_3)_4(NO_3)_2$ was the source of Pd for both cases. For the preparation of the impregnated catalyst, this was carried out via the incipient wetness method; i.e., the $Pd(NH_3)_4(NO_3)_2$ solution was prepared at the appropriate concentration such that as the solution is added to the mordenite there is just sufficient solution to wet the pores of the zeolite. The Pd solution is added to a beaker containing the dried mordenite dropwise, and the solid is continually stirred until the addition of the Pd solution is complete. Drying, calcination, and reduction of both catalysts are as described previously. The data show comparable performance between the two catalysts, in fact the loss of ring methyl groups and loss of total aromatics is lower with the impregnated catalyst, a desirable result. This difference reflects the activity of the catalyst, with the 1 wt. % Pd/mordenite catalyst prepared by ion exchange being somewhat more active. This is seen most clearly by consideration of the deactivation parameter, a, which has been described above, and is provided also in Table 9. It appears that the catalyst prepared via ion exchange has some advantage in terms of lower deactivation compared with the catalyst prepared via impregnation.

TABLE 9

|  | 1 % Pd/ mordenite Ion exchange prep | | 1 % Pd/ mordenite Impregnation prep | |
|---|---|---|---|---|
| Reaction Temperature, K. | 673 | | 673 | |
| Reaction Pressure, psig | 290 | | 290 | |
| WHSV, hr-1 | 3 | | 3 | |
| H2/hydrocarbon, mol/mol | 3.6 | | 3.4 | |
| Bz/C9 wt./wt. | 0.5 | | 0.5 | |
|  | 2 hours | 16 hours | 2 hours | 6 hours |
| Conversion, % | | | | |
| Benzene | 53.0 | 46.2 | 52.1 | 50.4 |
| Trimethylbenzenes | 81.9 | 83.2 | 82.4 | 81.3 |
| Ethyltoluenes | 98.1 | 97.5 | 97.1 | 95.8 |
| Product yields, mole % on feed | | | | |
| Methane | 0.5 | 0.4 | 0.4 | 0.3 |
| Ethane | 23.2 | 19.8 | 22.3 | 18.9 |
| C3+ C4 saturates | 16.0 | 12.9 | 11.1 | 8.7 |
| Toluene | 38.7 | 40.9 | 39.6 | 40.5 |
| Xylenes | 23.8 | 23.6 | 24.8 | 25.7 |
| C10+ aromatics | 1.2 | 1.2 | 1.1 | 1.2 |
| Loss of ring methyl groups, % | 5.0 | 4.5 | 5.9 | 2.2 |
| Loss of ring ethyl groups, % | 92.8 | 91.5 | 90.5 | 87.3 |
| Loss of aromatic rings, % | 10.0 | 5.2 | 7.1 | 3.5 |
| Deactivation parameter, α | | | | |
| Benzene | | 0.0062 | | 0.0077 |
| Trimethylbenzene | | 0.0001 | | 0.0033 |
| Ethyltoluene | | 0.0005 | | 0.0034 |

EXAMPLE 9

Establishing the Optimal Pd Metal Loading

A study was made for transalkylation of benzene/$C_9$ feedstock using variable concentrations of Pd, prepared via ion exchange, using standard dealuminated mordenite (Si/Al=16) prepared as described above in Section B. The comparative data are provided in Table 10. The data indicate that a Pd loading of 0.4 wt. % or greater is required for adequate performance of the catalyst under the standard operating conditions set forth above in Section C. Loadings above 1% show no significant advantage in terms of performance; however, higher loadings do not adversely affect performance. A fairly broad range of Pd loadings can be accommodated without adverse effect, above a minimum value of approximately 0.4 wt. %.

TABLE 10

Comparative performance of Pd/dealuminated mordenite at various Pd loadings

| | | | | | |
|---|---|---|---|---|---|
| Reaction Temperature, K. | 673 | 673 | 673 | 673 | 673 |
| Reaction Pressure, psig | 290 | 290 | 290 | 290 | 290 |
| WHSV, hr-1 | 3 | 3 | 3 | 3 | 3 |
| H2/hydrocarbon, mol/mol | 3.6 | 3.6 | 3.6 | 3.6 | 3.6 |
| Bz/C9 wt./wt. | 0.5 | 0.5 | 0.5 | 0.5 | 0.5 |
| Pd loading, wt. % | 0.2 | 0.4 | 1 | 2 | 5 |
| Reaction time = 16 hours | | | | | |
| Conversion, % | | | | | |
| Benzene | 41.2 | 42.0 | 46.2 | 41.5 | 49.4 |
| Trimethylbenzenes | 70.2 | 81.0 | 83.2 | 74.5 | 81.8 |
| Ethyltoluenes | 82.3 | 93.3 | 97.5 | 87.6 | 96.8 |
| Product yields, mole % on feed | | | | | |
| Methane | 0.4 | 0.4 | 0.4 | 0.5 | 0.4 |
| Ethane | 7.5 | 14.6 | 19.8 | 11.8 | 18.4 |
| C3 + C4 saturates | 6.4 | 8.6 | 12.9 | 7.6 | 11.3 |
| Toluene | 31.2 | 39.6 | 40.9 | 35.2 | 41.0 |
| Xylenes | 22.9 | 23.7 | 23.6 | 23.2 | 24.7 |
| C10+ aromatics | 3.2 | 1.7 | 1.2 | 2.3 | 1.4 |
| Loss of ring methyl groups, % | 0.0 | 2.3 | 4.5 | 0.0 | 0.3 |
| Loss of ring ethyl groups, % | 52.8 | 81.3 | 91.5 | 68.6 | 86.6 |
| Loss of aromatic rings, % | 0.8 | 1.7 | 5.2 | 1.4 | 4.3 |
| Deactivation parameter, α | | | | | |
| Benzene | 0.0038 | 0.0054 | 0.0062 | 0.0053 | 0.0038 |
| Trimethylbenzene | 0.0084 | 0.0013 | 0.0001 | 0.0048 | 0.0003 |
| Ethyltoluene | 0.0042 | 0.0021 | 0.0005 | 0.0037 | 0.0006 |

EXAMPLE 10

Preparation of 1% Pd/Dealuminated Catalyst Comprising a Silica Binder

In a comparative study, dealuminated mordenite catalyst (Si/Al=16) was alternatively mixed with a silica or alumina binder, followed by extruding and calcination at 550° C. The extruded catalyst binder was then ion exchanged with a solution of $NH_4OH$ (to prepare the ammonium form of the zeolite), followed by ion exchange with $Pd(NH_3)_4(NO_3)_2$. These catalysts, containing approximately 1% by weight Pd based on zeolite fraction only (hence, <1% based on total catalyst weight) were calcined at 550° C. in air and reduced in flowing hydrogen at 400° C. and evaluated for transalkylation of benzene/$C_9$ feedstock under, first, standard conditions and then conditions designed to accelerate the aging of the catalyst. The accelerated aging conditions entailed: increasing the reaction temperature from 400 to 415° C., and reducing the ratio of $H_2$/hydrocarbon in the feed from 3 to 1. Table 11 summarizes the comparative performance of the 1 wt. % Pd/mordenite, with no binder and with silica and alumina binders, both after a standard 8 hour run and after a 96 hour run at accelerated aging conditions, which has been found to be equivalent to operating on stream for approximately 1000 hours under standard conditions. The accelerated aging test differs from standard test in that higher reaction temperatures and lower $H_2$/hydrocarbon ratios are utilized. The performance with the silica binder is dearly superior to the alumina binder case and comparable to the performance of the 1 wt. % Pd/mordenite catalyst alone. In the case of the 1 wt. % Pd/mordenite plus alumina binder, the more rapid deactivation of the catalyst and poorer performance is dearly evident under the accelerated aging test conditions.

TABLE 11

|  | 1% Pd/mordenite with no binder | | 1% Pd/mordenite with 30% silica binder | | 1% Pd/mordenite with 30% alumina binder | |
| --- | --- | --- | --- | --- | --- | --- |
| Reaction Temperature, K. | 673 | 688 | 673 | 688 | 673 | 688 |
| Reaction Pressure, psig | 290 | 290 | 290 | 290 | 290 | 290 |
| WHSV, hr-1 | 3 | 3 | 3 | 3 | 3 | 3 |
| H2/hydrocarbon, mol/mol | 3 | 1 | 3 | 1 | 3 | 1 |
| Bz/C9 wt./wt. | 0.5 | 0.5 | 0.5 | 0.5 | 0.5 | 0.5 |
| Reaction time | 8 hours | 98 hours | 8 hours | 98 hours | 8 hours | 96 hours |
| Conversion, % | | | | | | |
| Benzene | 58 | 49 | 55 | 54 | 56 | 47 |
| Trimethylbenzenes | 81 | 74 | 81 | 76 | 80 | 67 |
| Ethyltoluenes | 98 | 89 | 97 | 87 | 96 | 81 |
| Product yields, mole % on feed | | | | | | |
| Toluene | 41 | 36 | 42 | 37 | 41 | 31 |
| Xylenes | 27 | 26 | 28 | 26 | 27 | 23 |
| C1–C6 saturates | 39 | 22 | 28 | 23 | 31 | 19 |
| Loss of aromatic rings, % | 7 | 2 | 3 | 3 | 4 | 2 |

EXAMPLE 11

Demonstration of High Toluene Yields Through the Use of Benzene/$C_9$ Feedstocks Containing High Content of Benzene in the Feed It is possible to achieve substantial selectivities and yields of toluene through the use of benzene/$C_9$ feedstocks containing high fractions of benzene. Benzene weight fractions exceeding 50 wt % can be used, to as high as 85 wt. %, without adverse affect on the catalyst. A catalyst comprising 1 wt % Pd/dealuminated mordenite, prepared similarly to methods described in Example 1, was utilized in these experiments. The particular sample of dealuminated mordenite used in these experiments had a Si/Al atomic ratio of 19.4. Catalyst testing was as in Example 1, but with the modification in the ratio of benzene/$C_9$ in the feed. Of particular interest in these experiments is the selectivity of the product toward toluene. Toluene selectivity is defined as:

Toluene Selectivity (%)=(wt Toluene in Product)/(wt Toluene+wt Ethylbenzene+wt Xylene+wt $C_{11}$ Aromatics in Product)×100 where the $C_{10}$ product is excluded from the calculation due to its presence in the feed at higher concentration than in the product. The results are summarized in Table 12.

TABLE 12

| Reaction Temperature, K. | 673 | 673 | 673 |
| --- | --- | --- | --- |
| Reaction Pressure, kg/cm2 | 20 | 20 | 20 |

TABLE 12-continued

| WHSV, hr-1 | 3 | 3 | 3 |
| --- | --- | --- | --- |
| H2/hydrocarbon, mol/mol | 3 | 3 | 3 |
| Benzene wt % in feed | 70.8 | 59.6 | 48.5 |
| Conversion, % | | | |
| Benzene | 36.3 | 36.4 | 36.9 |
| Trimethylbenzenes | 94.5 | 96.4 | 92.4 |
| Ethyltoluenes | 95.8 | 97.7 | 97.0 |
| Product composition, wt % | | | |
| Methane | 0.1 | 0.1 | 0.1 |
| Ethane | 4.9 | 5.4 | 6.8 |
| C3 + C4 saturates | 4.3 | 5.4 | 4.7 |
| Toluene | 34.0 | 38.7 | 38.2 |
| Xylenes | 8.7 | 9.3 | 15.2 |
| Ethylbenzene | 1.0 | 0.8 | 0.9 |
| C10 aromatics | 0.2 | 0.0 | 0.2 |
| C11 aromatics | 0.3 | 0.6 | 0.3 |
| Toluene selectivity | 77.3 | 78.3 | 70 |

We claim as our invention:

1. A process for the conversion of a mixed aromatic hydrocarbon starting material, containing at least about 20 mole percent of $C_9$ aromatic compounds which are ring substituted with ethyl or higher alkyl groups, into an aromatic hydrocarbon product, which is enriched in toluene and/or xylenes content relative to the starting material and reduced in toluene and $C_9$ aromatic content relative to the starting material, which comprises contacting in a reaction zone, the starting material with a catalytically-effective amount of a catalyst consisting essentially of palladium on a dealuminated mordenite having a Si/Al atomic ratio of about 12 to 30, said palladium being loaded onto the mordenite in salt form and subject to calcination at a temperature not exceeding about 500° C. In the presence of an oxygen-containing gas to convert the palladium salt into an oxide, and said contacting of the starting material and catalyst occurring in the presence of hydrogen and under temperature and pressure conditions to effect the conversion of said staring material to the product and recovering the product from the reaction zone.

2. The process of claim 1 wherein the aromatic hydrocarbon starting material contains about 20 to about 50 mole percent of ethyltoluene.

3. The process of claim 2 wherein the aromatic hydrocarbon starting material contains at least 33 mole percent benzene.

4. The process of claim 3 wherein the aromatic hydrocarbon starting material contains from 50 to 80 mole percent benzene and the product is enriched in toluene.

5. The process of claim 1 wherein the dealuminated mordenite contains essentially no extra-framework aluminum.

6. The process of claim 5 wherein the palladium is present on the mordenite at a concentration of between about 0.3 and about 2.0 weight percent of the total mordenite weight.

7. The process of claim 6 wherein the dealuminated mordenite is prepared from a non-dealuminated precursor by the sequential steps of steaming of the non-dealuminated precursor followed by acid wash of the steamed precursor.

8. The process of claim 6 wherein the dealuminated mordenite has a Si/Al ratio of about 14 to about 28 and the palladium is present at a concentration of about one weight percent.

9. The process of claim 6 wherein the dealuminated mordenite contains a non-acidic binder.

10. The process of claim 9 wherein the catalyst contains between about 10 to about 50 percent by weight of a silica binder based on the total weight of mordenite plus binder.

11. The process of claim 10 wherein the silica binder is present at between about 25 and about 35 percent by weight of mordenite plus binder.

* * * * *